US009468453B2

(12) United States Patent
Hart et al.

(10) Patent No.: US 9,468,453 B2
(45) Date of Patent: Oct. 18, 2016

(54) ENDOSCOPIC SURGICAL FORCEPS

(71) Applicant: COVIDIEN LP, Mansfield, MA (US)

(72) Inventors: Keir Hart, Lafayette, CO (US); Mark J. Huseman, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 324 days.

(21) Appl. No.: 14/182,894

(22) Filed: Feb. 18, 2014

(65) Prior Publication Data
US 2014/0330308 A1 Nov. 6, 2014

Related U.S. Application Data (60) Provisional application No. 61/819,325, filed on May 3, 2013.

(51) Int. Cl.
*A61B 17/29* (2006.01)
*A61B 18/14* (2006.01)

(52) U.S. Cl.
CPC ........... *A61B 17/29* (2013.01); *A61B 18/1445* (2013.01); *A61B 2017/292* (2013.01); *A61B 2017/2917* (2013.01); *A61B 2017/2919* (2013.01); *A61B 2017/2936* (2013.01); *A61B 2018/1455* (2013.01)

(58) Field of Classification Search
CPC .............. A61B 17/29; A61B 18/1445; A61B 2017/2917; A61B 2017/292; A61B 2017/2936; A61B 2018/1455; A61B 2017/2919
See application file for complete search history.

(56) References Cited

U.S. PATENT DOCUMENTS

| 1,659,112 | A | 2/1928 | Littlejohn |
| D249,549 | S | 9/1978 | Pike |
| D263,020 | S | 2/1982 | Rau, III |
| 4,522,207 | A | 6/1985 | Klieman et al. |
| D295,893 | S | 5/1988 | Sharkany et al. |
| D295,894 | S | 5/1988 | Sharkany et al. |

(Continued)

FOREIGN PATENT DOCUMENTS

| CN | 201299462 | | 9/2009 |
| DE | 2415263 | A1 | 10/1975 |

(Continued)

OTHER PUBLICATIONS

U.S. Appl. No. 13/731,674, filed Dec. 31, 2012; inventor: Siebrecht.

(Continued)

*Primary Examiner* — Julian W Woo (57) ABSTRACT

A surgical instrument includes an end effector assembly, first and second handles, and a drive assembly. The handles are pivotable relative to one another between a spaced-apart position and an approximated position. The drive assembly includes a drive bar and a biasing member. The drive bar is coupled to the end effector assembly such that translation of the drive bar effects movement of the end effector assembly between first and second positions. First and second ends of the biasing member are coupled to the respective first and second handles. An intermediate portion of the biasing member is coupled to the drive bar such that movement of the handles from the spaced-apart to the approximated position displaces the intermediate portion and urges the drive bar to translate relative to the end effector assembly to effect movement of the end effector assembly between the first and second positions.

11 Claims, 7 Drawing Sheets

(56) References Cited

U.S. PATENT DOCUMENTS

| | | | |
|---|---|---|---|
| D298,353 S | 11/1988 | Manno | |
| D299,413 S | 1/1989 | DeCarolis | |
| 5,133,727 A | 7/1992 | Bales et al. | |
| 5,238,002 A | 8/1993 | Devlin et al. | |
| 5,269,804 A | 12/1993 | Bales et al. | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,413,583 A * | 5/1995 | Wohlers | A61B 17/0469 606/148 |
| 5,575,805 A * | 11/1996 | Li | A61B 17/29 606/174 |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| 7,083,618 B2 * | 8/2006 | Couture | A61B 18/1445 606/49 |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| 7,364,582 B2 | 4/2008 | Lee | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 8,430,876 B2 | 4/2013 | Kappus et al. | |
| 8,585,736 B2 | 11/2013 | Horner et al. | |
| 2006/0079933 A1* | 4/2006 | Hushka | A61B 17/2909 606/205 |
| 2007/0106297 A1 | 5/2007 | Dumbauld et al. | |
| 2010/0204697 A1 | 8/2010 | Dumbauld et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |

(56) References Cited

FOREIGN PATENT DOCUMENTS

| | | | |
|---|---|---|---|
| JP | 2008-054926 A | 3/2008 | |
| JP | 2011125195 A | 6/2011 | |
| SU | 401367 A1 | 11/1974 | |
| WO | 0036986 A1 | 6/2000 | |
| WO | 0059392 A1 | 10/2000 | |
| WO | 0115614 A1 | 3/2001 | |
| WO | 0154604 A1 | 8/2001 | |
| WO | 02045589 A3 | 9/2002 | |
| WO | 2006/021269 A1 | 3/2006 | |
| WO | 2005110264 A3 | 4/2006 | |
| WO | 2008/040483 A1 | 4/2008 | |
| WO | 2011/018154 A1 | 2/2011 | |

OTHER PUBLICATIONS

U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.

(56) References Cited

OTHER PUBLICATIONS

Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.

\* cited by examiner

ENDOSCOPIC SURGICAL FORCEPS

CROSS REFERENCE TO RELATED APPLICATION

The present application claims the benefit of and priority to U.S. Provisional Application Ser. No. 61/819,325, filed on May 3, 2013, the entire contents of which are incorporated herein by reference.

BACKGROUND

1. Technical Field

The present disclosure relates to surgical instruments and, more particularly, to an endoscopic surgical forceps configured for treating and/or cutting tissue.

2. Background of Related Art

A surgical forceps is a plier-like device which relies on mechanical action between its jaws to grasp, clamp, and constrict tissue. Energy-based surgical forceps utilize both mechanical clamping action and energy to affect hemostasis by heating tissue to coagulate and/or cauterize tissue. Certain surgical procedures require more than simply cauterizing tissue and rely on the unique combination of clamping pressure, precise energy control and gap distance (i.e., distance between opposing jaw members when closed about tissue) to "seal" tissue. Typically, once tissue is sealed, the surgeon has to accurately sever the tissue along the newly formed tissue seal. Accordingly, many tissue sealing devices have been designed which incorporate a knife or blade member which effectively severs the tissue after forming a tissue seal.

As an alternative to open forceps for use with open surgical procedures, many modern surgeons use endoscopic or laparoscopic instruments for remotely accessing tissue through smaller, puncture-like incisions or natural orifices. As a direct result thereof, patients tend to benefit from less scarring and reduced healing time. Endoscopic instruments are typically inserted into the patient through a cannula, or port. Smaller cannulas are usually preferred, which, as can be appreciated, ultimately present a design challenge to instrument manufacturers who must find ways to make endoscopic instruments that fit through the smaller cannulas without compromising functionality.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with the present disclosure, a surgical instrument is provided. The surgical instrument includes an end effector assembly, first and second handles, and a drive assembly. The end effector assembly is movable between a first position and a second position. The first and second handles are pivotable about the first ends thereof and extend to the second ends thereof. The second ends of the handles are movable relative to one another between a spaced-apart position and an approximated position. The drive assembly includes a drive bar and a biasing member. The drive bar is coupled to the end effector assembly at a distal end of the drive bar such that translation of the drive bar relative to the end effector assembly effects movement of the end effector assembly between the first and second positions. The biasing member defines a first end, a second end, and an intermediate portion disposed between the first and second ends. The first end of the biasing member is coupled to the first handle adjacent the second end of the first handle. The second end of the biasing member is coupled to the second handle adjacent the second end of the second handle. The intermediate portion of the biasing member is coupled to the drive bar. As such, movement of the handles from the spaced-apart position to the approximated position urges the first and second ends of the biasing member towards one another such that the intermediate portion of the biasing member is displaced relative to the first and second ends of the biasing member. Displacement of the intermediate portion, in turn, urges the drive bar to translate relative to the end effector assembly to effect movement of the end effector assembly between the first and second positions.

In an aspect of the present disclosure, the end effector assembly includes a pair of jaw members. One or both of the jaw members is movable relative to the other between an open position, corresponding to the first position, and a closed position, corresponding to the second position, for grasping tissue therebetween.

In another aspect of the present disclosure, the biasing member is configured such that a closure pressure within the range of about 3 kg/cm$^2$ to about 16 kg/cm$^2$ is imparted to tissue grasped between the jaw members.

In still aspect of the present disclosure, one or both of the jaw members is adapted to connect to a source of energy for conducting energy through tissue grasped between the jaw members to treat tissue.

In yet another aspect of the present disclosure, the surgical instrument further includes a housing. In such aspects, the first and second handles are pivotably coupled to the housing at the first ends thereof. The second ends of the handles are movable relative to one another and the housing between the spaced-apart position and the approximated position.

In still yet another aspect of the present disclosure, a shaft extends distally from the housing and includes the end effector assembly disposed at a distal end of the shaft. In such aspects, the drive bar may extend from the housing distally through the shaft.

In another aspect of the present disclosure, in the spaced-apart position of the handles, the biasing member defines a proximally-bowed configuration wherein the intermediate portion is proximally offset relative to the first and second ends of the biasing member by a first distance. Additionally or alternatively, in the approximated position of the handles, the biasing member may be further bowed-proximally such that the intermediate portion is proximally offset relative to the first and second ends of the biasing member by a second distance greater than the first distance.

In an aspect of the present disclosure, a mandrel is coupled to the drive bar at a proximal end of the drive bar. The mandrel is disposed in abutting relation relative to the intermediate portion of the biasing member such that displacement of the intermediate portion urges the mandrel to translate, thereby urging the drive bar to translate relative to the end effector assembly.

In another aspect of the present disclosure, the mandrel is biased towards an initial position, thereby biasing the end effector assembly towards the first position.

In accordance with aspects of the present disclosure a surgical instrument is provided including an end effector assembly, first and second handles, and a drive assembly. The end effector assembly is movable between a first position and a second position. The handles are pivotable about the first ends thereof and extend to the second ends thereof.

The second ends of the handles are movable relative to one another between a spaced-apart position and an approximated position. The drive assembly includes a drive bar, first and second linkages, and first and second cables. The drive bar is coupled to the end effector assembly at a distal end of the drive bar such that translation of the drive bar relative to the end effector assembly effects movement of the end effector assembly between the first and second positions. The first ends of the linkages are pivotably coupled to the respective first and second handles adjacent the second ends of the first and second handles. The first cable member is coupled between a second end of the first linkage and the drive bar, while the second cable member is coupled between a second end of the second linkage and the drive bar. As such, movement of the handles from the spaced-apart position to the approximated position pivots the first and second linkages relative to the drive bar between a more-angled orientation and a more-aligned orientation, thereby urging the first and second cable members to translate such that the drive bar is translated relative to the end effector assembly to effect movement of the end effector assembly between the first and second positions.

In an aspect of the present disclosure, the end effector assembly includes a pair of jaw members. One or both of the jaw members is movable relative to the other between an open position, corresponding to the first position, and a closed position, corresponding to the second position, for grasping tissue therebetween. The cable members may be resiliently extendable along the lengths thereof and are configured such that a closure pressure within the range of about 3 kg/cm$^2$ to about 16 kg/cm$^2$ is imparted to tissue grasped between the jaw members.

In another aspect of the present disclosure, one or both of the jaw members is adapted to connect to a source of energy for conducting energy through tissue grasped between the jaw members to treat tissue.

In still another aspect of the present disclosure, the surgical instrument further includes a housing. In such aspects, the first and second handles are pivotably coupled to the housing at the first ends thereof. The second ends of the handles movable relative to one another and the housing between the spaced-apart position and the approximated position.

In yet another aspect of the present disclosure, the housing defines first and second tracks that receive the first and second cables. The tracks are configured to guide translation of the cables.

In still yet another aspect of the present disclosure, a shaft extends distally from the housing and includes the end effector assembly disposed at a distal end of the shaft. In such aspects, the drive bar may extend from the housing distally through the shaft.

In another aspect of the present disclosure, a mandrel is coupled to the drive bar at a proximal end of the drive bar. In such aspects, the first and second cable members coupled to the mandrel such that translation of the cable members urges the mandrel to translate, thereby urging the drive bar to translate relative to the end effector assembly.

BRIEF DESCRIPTION OF THE DRAWINGS

Various aspects and features of the present disclosure described herein with reference to the drawings wherein.

DETAILED DESCRIPTION

Figure 1A:
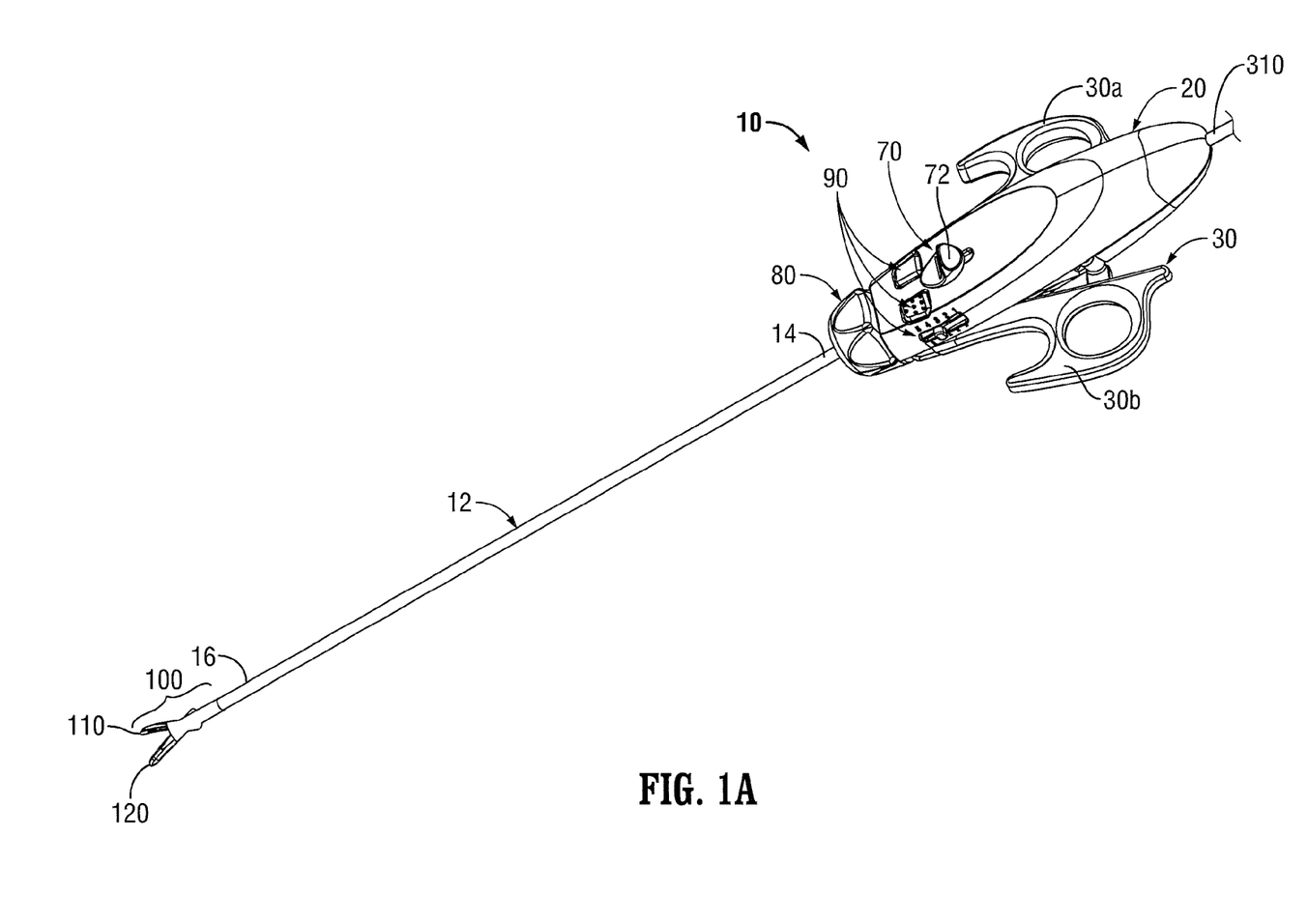
FIG. 1A is a top, perspective view of a surgical forceps provided in accordance with the present disclosure, wherein an end effector assembly of the surgical forceps is shown in an open configuration.
Figure 1B:
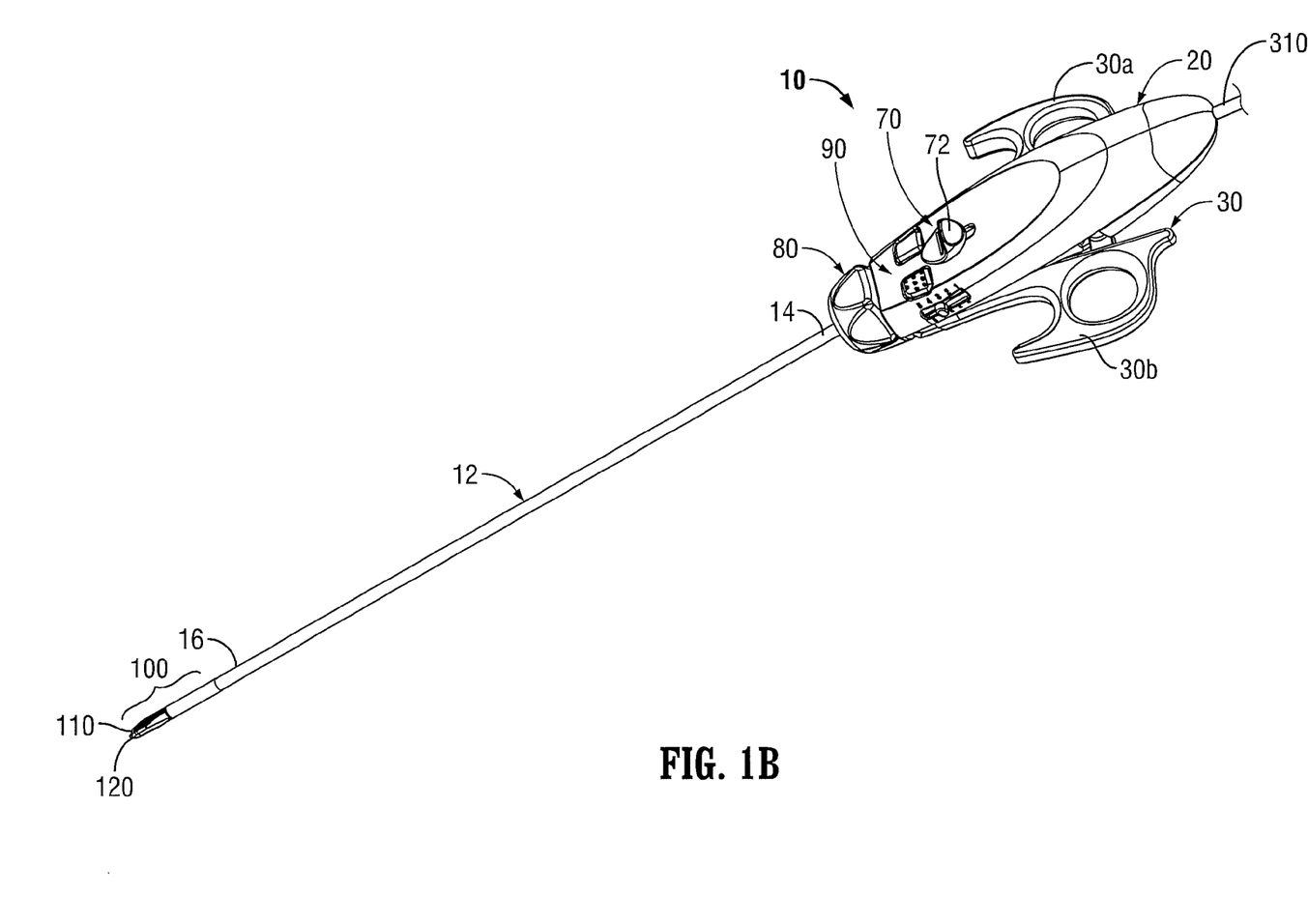
FIG. 1B is a top, perspective view of the surgical forceps of FIG. 1A wherein the end effector assembly is shown in a closed configuration.
Figure 2:
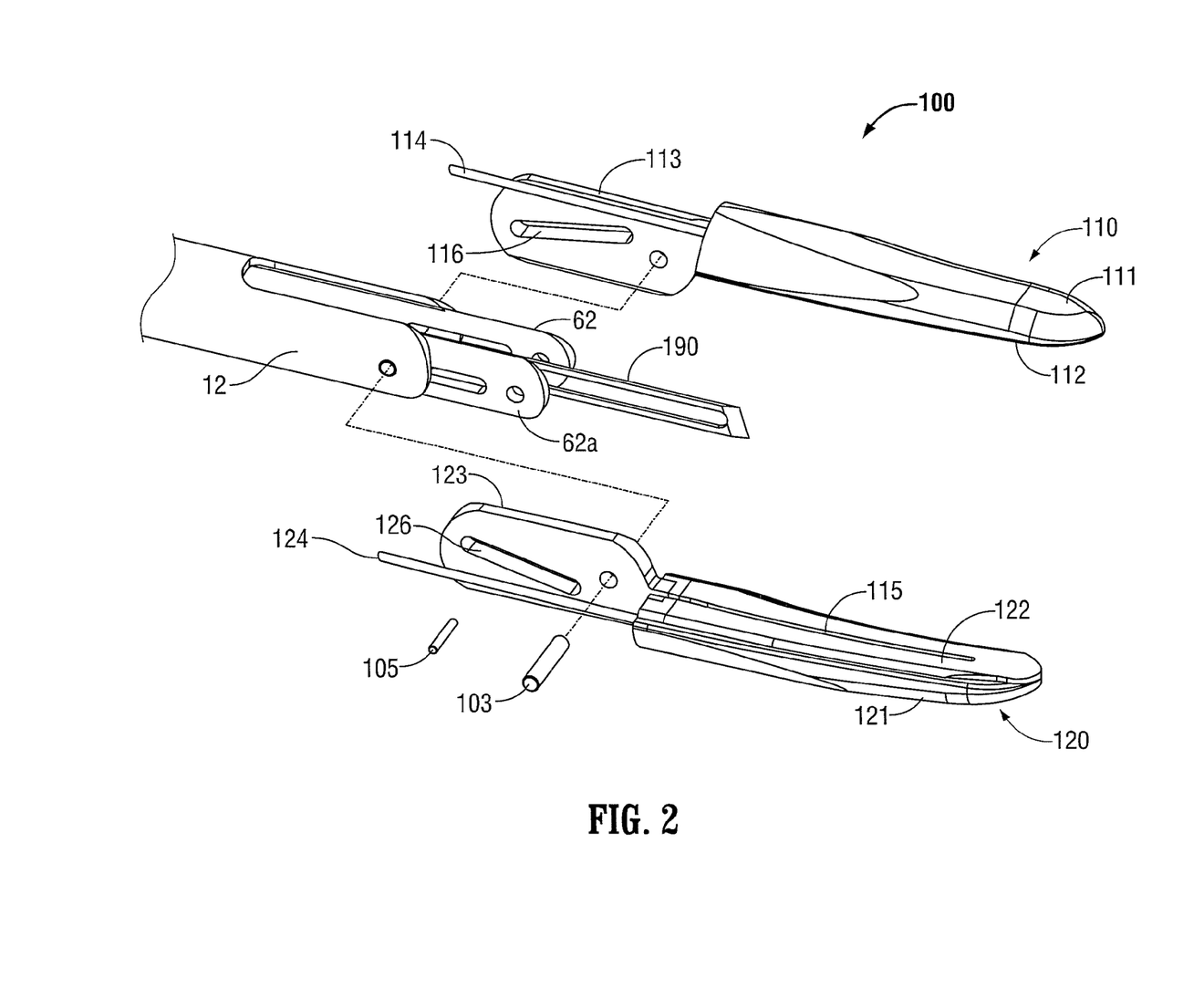
FIG. 2 is an enlarged, side, perspective, view of the end effector assembly of the surgical forceps of FIG. 1A, shown with parts separated.

Turning now to FIGS. 1A-2, one embodiment of a surgical forceps configured for use in accordance with the present disclosure is shown generally identified by reference numeral 10. Although surgical forceps 10 is shown configured for use in connection with endoscopic surgical procedures, the present disclosure is equally applicable for use in more traditional open surgical procedures and with any suitable surgical instrument. For the purposes herein, forceps 10 is generally described.

Forceps 10 is adapted for use in various surgical procedures and generally includes a housing 20, a handle assembly 30, a trigger assembly 70, a rotating assembly 80, an activation assembly 90, and an end effector assembly 100 which mutually cooperate to grasp, treat, and/or cut tissue. Forceps 10 further includes a shaft 12 having a distal end 16 that mechanically engages end effector assembly 100 and a proximal end 14 that mechanically engages housing 20. A cable 310 is adapted to connect forceps 10 to a source of energy, e.g., a generator (not shown), although forceps 10 may alternatively be configured as a battery powered instrument.

Handle assembly 30 includes two movable handles 30a and 30b disposed on opposite sides of housing 20. Handles 30a and 30b are movable relative to one another to actuate end effector assembly 100, as will be described in greater detail below. Rotating assembly 80 is mechanically coupled to housing 20 and is rotatable in either direction to rotate shaft 12 and, thus, end effector assembly 100. Such a configuration allows end effector assembly 100 to be rotated in either direction with respect to housing 20.

Continuing with reference to FIGS. 1A-2, end effector assembly 100 is attached at distal end 16 of shaft 12 and includes a pair of opposing jaw members 110 and 120. Handles 30a and 30b of handle assembly 30 ultimately connect to a drive assembly 60 (FIGS. 3A-3B) disposed within housing 20 and extending through shaft 12 which, together, cooperate to impart movement of jaw members 110 and 120 from an open position (FIG. 1A) wherein jaw members 110 and 120 are disposed in spaced relation relative to one another, to a closed position (FIG. 1B) wherein jaw members 110 and 120 cooperate to grasp tissue therebetween. Various embodiments of drive assemblies 60, 600 (FIGS. 3A-3B and 4A-4B, respectively) will be described in greater detail below.

With particular reference to FIG. 2, in conjunction with FIGS. 1A-1B, end effector assembly 100 includes first and second jaw members 110, 120, each including an outer insulative jaw housing 111, 121, an electrically-conductive tissue-contacting surface 112, 122, and a proximal flange 113, 123, respectively. Tissue-contacting surfaces 112, 122 are disposed about jaw housings 111, 121, respectively, and are electrically coupled to activation assembly 90 (FIG. 1) and the source of energy (not shown), e.g., via wires 114, 124, respectively, which extend from respective jaw members 110, 120 through shaft 12, such that energy may be selectively supplied to tissue-contacting surface 112 and/or tissue-contacting surface 122 and conducted therebetween and through tissue grasped between jaw members 110, 120 to treat, e.g., seal, tissue.

Proximal flanges 113, 123 of jaw members 110, 120 are pivotably coupled to one another and shaft 12 via a pivot pin 103. End effector assembly 100 is designed as a bilateral assembly, i.e., where both jaw member 110 and jaw member 120 are moveable about pivot 103 relative to one another and to shaft 12. However, end effector assembly 100 may alternatively be configured as a unilateral assembly, i.e., where one of the jaw members 110, 120 is fixed relative to shaft 12 and the other jaw member 110, 120 is moveable about pivot 103 relative to shaft 12 and the fixed jaw member 110, 120. Proximal flanges 113, 123 of jaw members 110, 120, respectively, each further include an oppositely-angled cam slot 116, 126 defined therethrough that is configured to receive a drive pin 105. Drive pin 105 is mounted at distal end 62a of drive bar 62 such that, as will be described in greater detail below, reciprocation of drive bar 62 through shaft 12 effects pivoting of jaw members 110, 120 relative to one another between the open and closed positions (FIGS. 1A and 1B, respectively). More specifically, cam slots 116, 126 are oriented such that proximal translation of drive pin 105 effects pivoting of jaw members 110, 120 from the open position towards the closed position and such that distal translation of drive pin 105 effects pivoting of jaw members 110, 120 from the closed position towards the open position.

A knife channel 115 extends longitudinally through one (or both) jaw members 110, 120, e.g., jaw member 120, to facilitate reciprocation of knife blade 190 between jaw members 110, 120 to cut tissue disposed therebetween, e.g., upon actuation of trigger 72 of trigger assembly 70 (see FIGS. 1A-1B). That is, knife blade 190 is operatively coupled to trigger assembly 70 such that actuation of trigger 72 advances knife blade 190 from a retracted position, wherein knife blade 190 is positioned proximally of jaw members 110, 120, to a deployed position, wherein knife blade 190 extends between jaw members 110, 120 and through channel 115 to cut tissue grasped between jaw members 110, 120. Knife blade 190 may be configured for mechanical cutting (as shown), or may be energizable, e.g., electrically coupled to the source of energy (not shown) via one or more wires (not shown), for electromechanically cutting tissue.

Figure 3A:
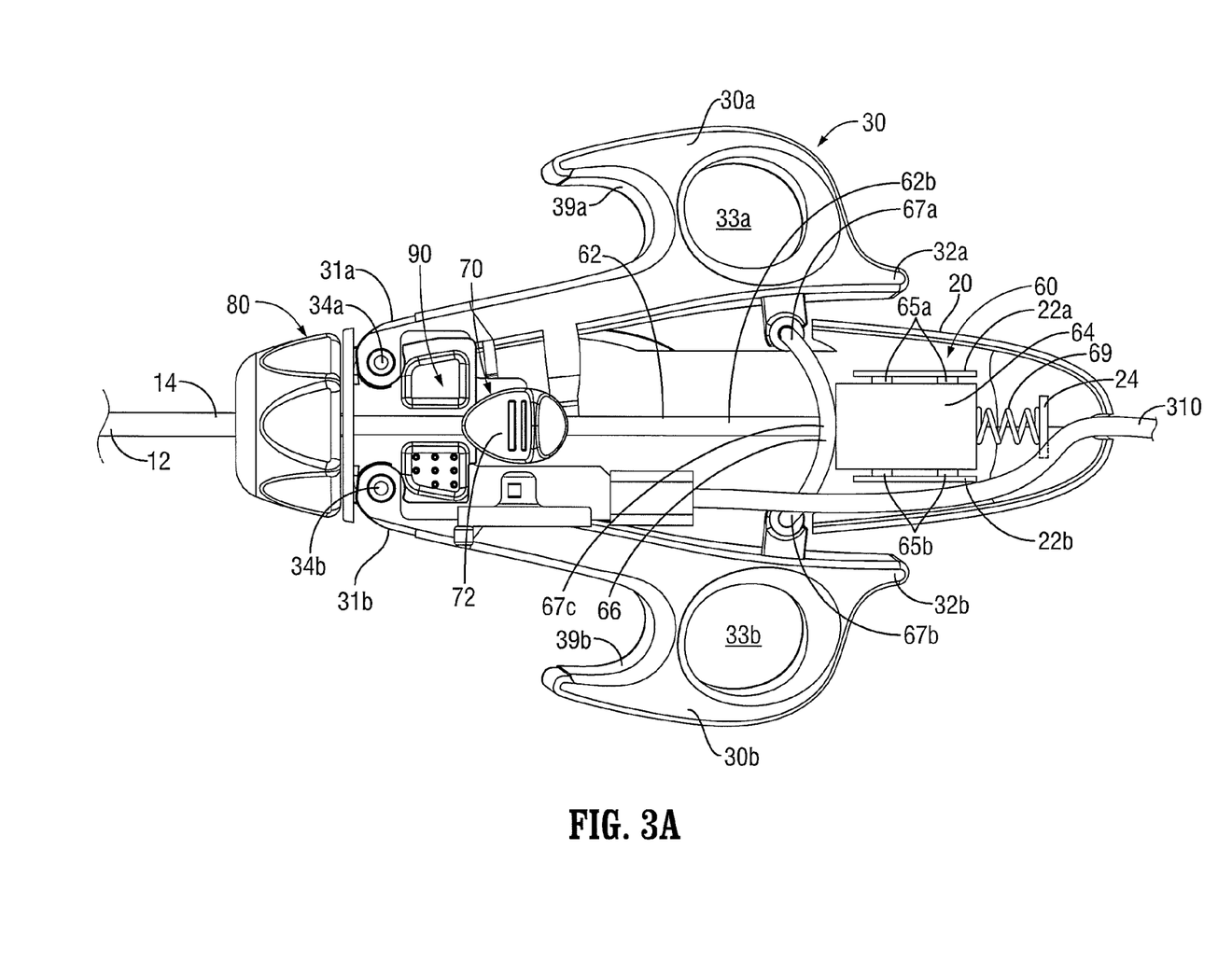
FIG. 3A is an enlarged, top view of the surgical forceps of FIG. 1A showing the disposition of the drive assembly when the end effector assembly is in the open configuration.
Figure 3B:
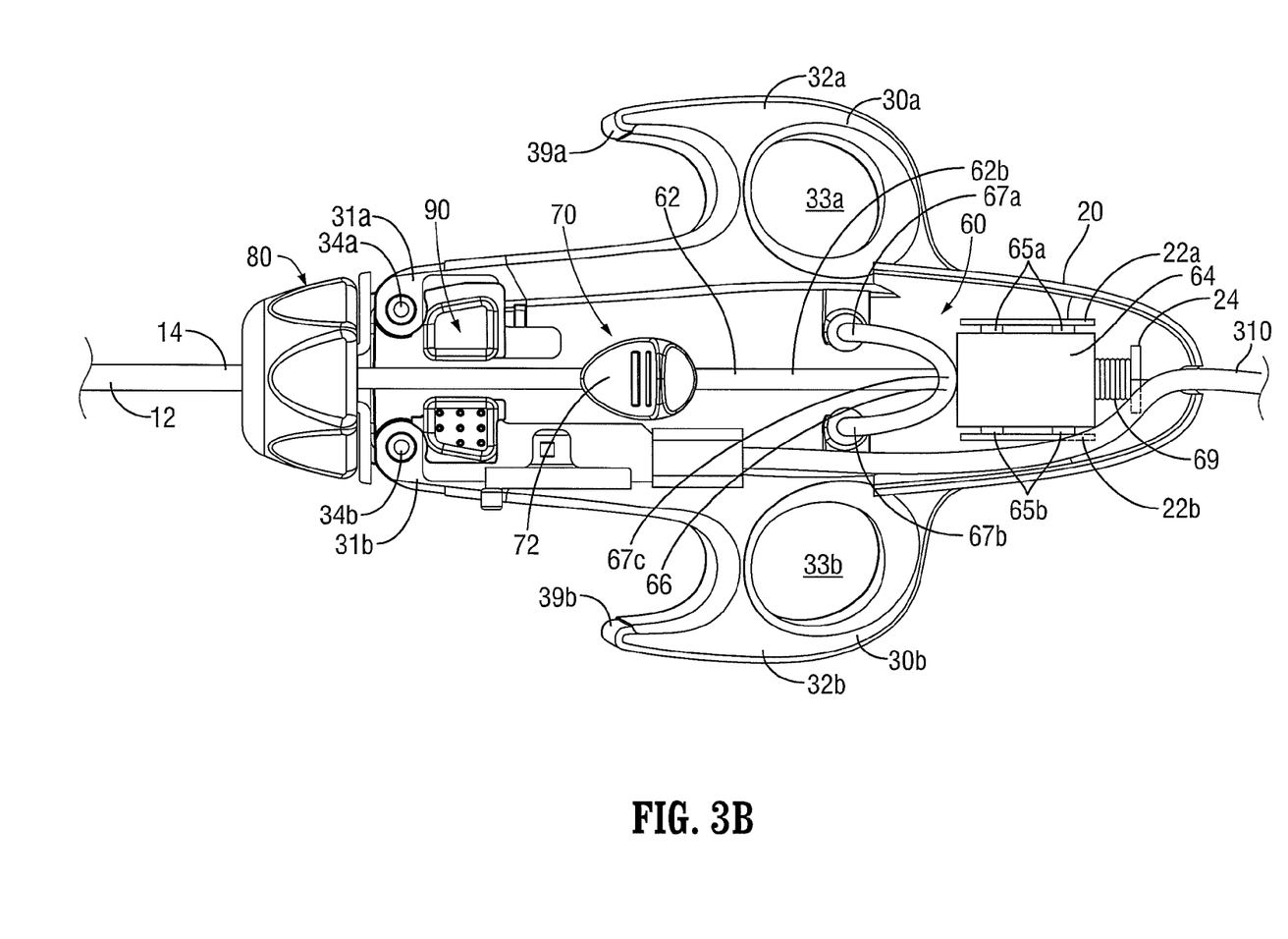
FIG. 3B is an enlarged, top view of the surgical forceps of FIG. 1A showing the disposition of the drive assembly when the end effector assembly is in the closed configuration.

Referring to FIGS. 3A-3B, in conjunction with FIGS. 1A-2, handles 30a and 30b of handle assembly 30 each include an aperture 33a and 33b, respectively, defined therein which enables a user to grasp and move handles 30a and 30b relative to one another and housing 20 between a spaced-apart position (FIG. 1A) and an approximated position (FIG. 1B). Handles 30a and 30b also include ergonomically-enhanced gripping elements 39a and 39b, respectively, disposed along an outer edge thereof which are designed to facilitate gripping of handles 30a and 30b. Gripping elements 39a and 39b may include one or more protuberances, scallops, ribs, or other features configured to enhance gripping. Handles 30a and 30b are pivotably coupled to housing 20 at their respective distal ends 31a, 31b via pivot pins 34a, 34b, respectively, and extend proximally to proximal ends 32a, 32b, respectively, thereof. As mentioned above, handles 30a, 30b are coupled to drive assembly 60 such that pivoting of handles 30a, 30b about pivot pins 34a, 34b, respectively, and relative to one another effects pivoting of jaw members 110, 120 between the open and closed positions (see FIGS. 1A and 1B, respectively).

Drive assembly 60 includes a drive bar 62 defining a proximal end 62b disposed within housing 20 and a distal end 62a (FIG. 2) that extends through shaft 12, ultimately coupling to jaw members 110, 120 via drive pin 105. A mandrel 64 disposed within housing 20 is engaged to the proximal end 62b of drive bar 62. Mandrel 64 includes one or more first tabs 65a and one or more second tabs 65b extending oppositely from mandrel 64 and engaged within tracks 22a, 22b, respectively, defined within housing 20 to guide translation of mandrel 64 and, thus, drive bar 62, relative to housing 20. Other suitable guide/alignment mechanisms are also contemplated. A spring 69 is positioned between the proximal end of mandrel 64 and a stop 24 disposed within housing 20 to bias mandrel 64 distally. As such, drive bar 62 and drive pin 105 are biased distally, thereby biasing jaw members 110, 120, towards the open position in the absence of actuation of handles 30a, 30b. As an alternative to spring 69, mandrel 64 may be coupled to intermediate portion 67c of biasing member 66 for biasing jaw members 110, 120 towards the open position. Biasing member 66 is described in detail below.

Drive bar 60 further includes a biasing member 66, e.g., a resiliently flexible band, flat spring, etc., coupled to each of handles 30a, 30b and positioned distally adjacent, e.g., in contact with, mandrel 64. More specifically, biasing member 66 is coupled to handle 30a towards proximal end 32a of handle 30a at a first end 67a of biasing member 66 and to handle 30b towards proximal end 32b of handle 30b at a second end 67b of biasing member 66, with intermediate portion 67c of biasing member 66 abutting mandrel 64. Biasing member 66 defines a proximally-bowed configuration at rest, as shown in FIG. 3A. That is, at rest, intermediate portion 67c of biasing member 66 is proximally offset relative to first and second ends 67a, 67b of biasing member 66.

In order to move jaw members 110, 120 from the open position to the closed position, handles 30a, 30b are squeezed, e.g., pivoted about pivot pins 34a, 34b, inwardly towards one another and housing 20. As handles 30a, 30b are pivoted in this manner, proximal ends 32a, 32b of handles 30a, 30b are approximated relative to housing 20 and one another. The approximation of proximal ends 32a, 32b of handles 30a, 30b towards one another urges first and second ends 67a, 67b of biasing member 66 inwardly towards one another such that biasing member 66 is bowed further proximally, e.g., such that intermediate portion 67c of biasing member 66 is further proximally offset relative to first and second ends 67a, 67b, as shown in FIG. 3B. Due to the abutment of intermediate portion 67c of biasing member 66 with mandrel 64, proximal movement of intermediate portion 67c urges mandrel 64 proximally, thereby pulling drive bar 62 proximally and pivoting jaw members 110, 120 from the open position (FIG. 1A) towards the closed position (FIG. 1B) to grasp tissue therebetween. The spring force of biasing member 66, alone or in conjunction with the spring force of spring 69 (in embodiments where spring 69 is provided), may be configured such that jaw members 110, 120 impart a closure pressure on tissue grasped therebetween within a range of about 3 kg/cm$^2$ to about 16 kg/cm$^2$, although other closure pressures are also contemplated.

With tissue grasped between jaw members 110, 120, energy may be supplied to tissue-contacting surfaces 112, 122 and conducted through tissue to treat, e.g., seal, tissue via activation of activation assembly 90. Additionally or as an alternative to tissue treatment, depending on a particular purposes, trigger 72 may be actuated to advance knife blade 190 between jaw members 110, 120 to cut the tissue grasped therebetween. Thereafter, jaw members 110, 120 may be moved back to the open position (FIG. 1A) to release the treated and/or cut tissue. More specifically, release or return of handles 30a, 30b to the spaced-apart position relative to one another and housing 20 allows biasing member 66 to return under bias back to its at-rest position, shown in FIG. 3A. Upon return of biasing member 66 to its at-rest position (and under the bias of spring 69, where so provided), mandrel 64 and drive bar 62 are returned distally such that drive pin 105 urges jaw members 110, 120 to pivot away from one another to the open position (FIG. 1A).

Figure 4A:
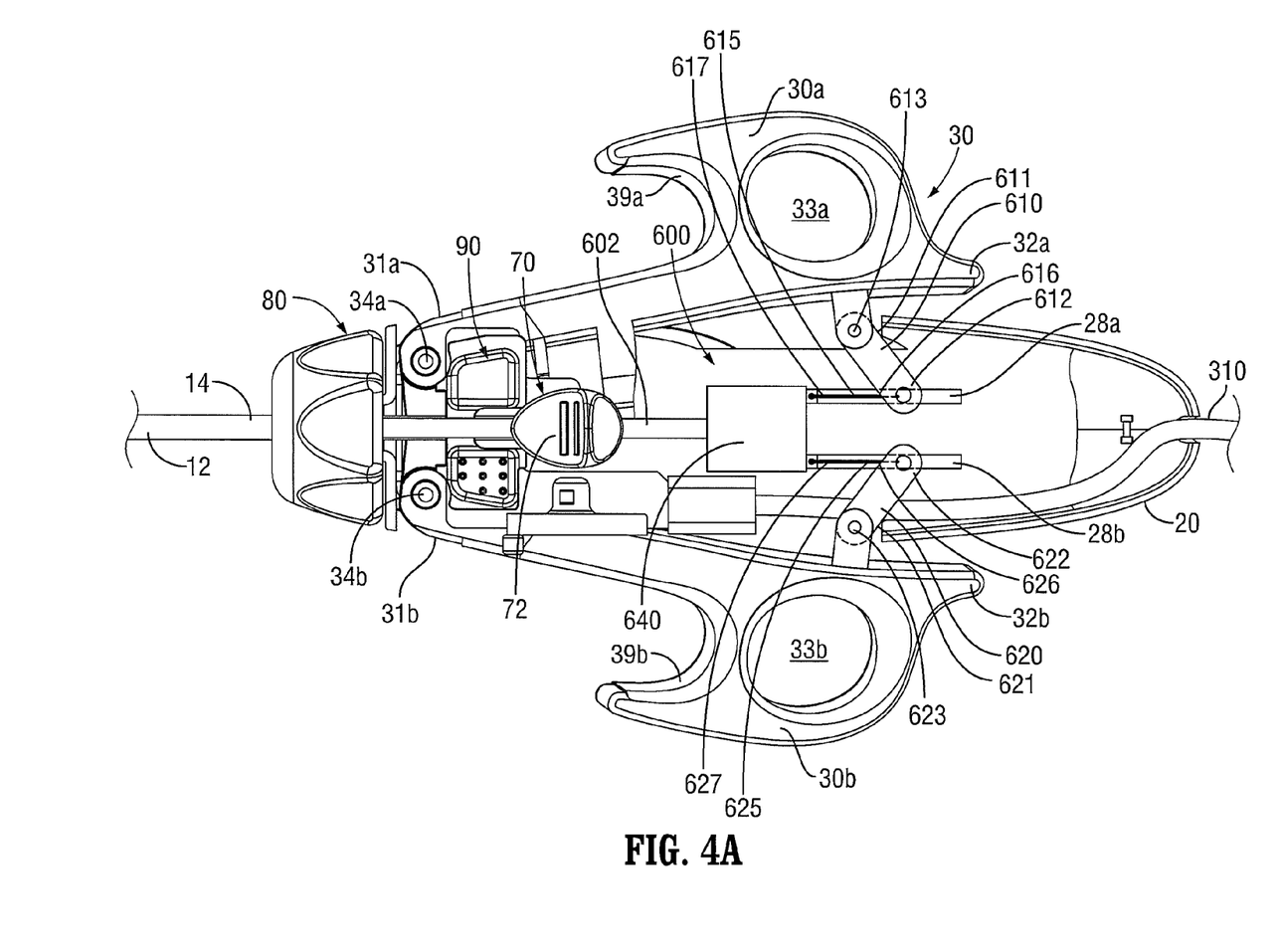
FIG. 4A is an enlarged, top view of the surgical forceps of FIG. 1A including another drive assembly, showing the disposition of the drive assembly when the end effector assembly is in the open configuration.
Figure 4B:
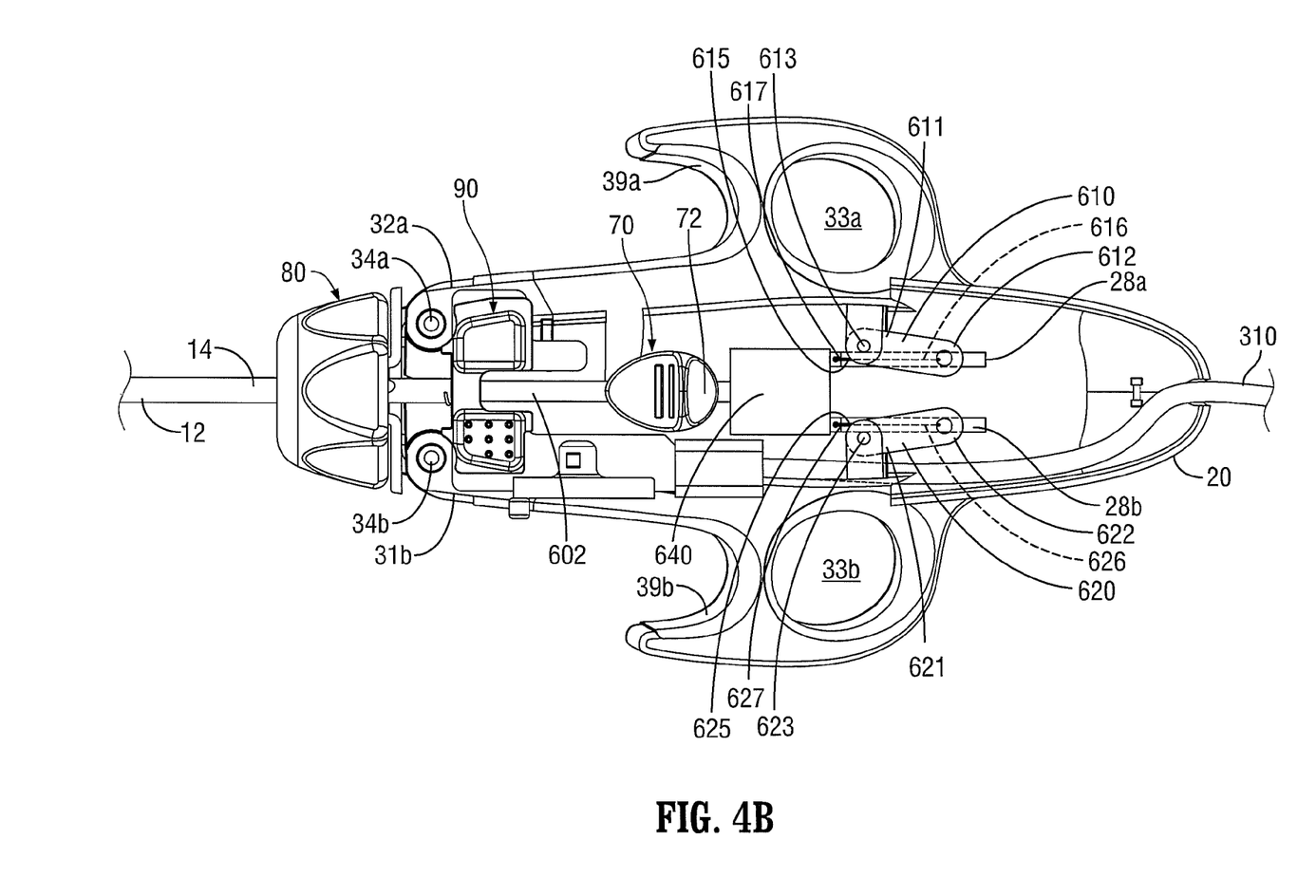
FIG. 4B is an enlarged, top view of the surgical forceps of FIG. 1A showing the disposition of the drive assembly of FIG. 4A when the end effector assembly is in the closed configuration.

Turning now to FIGS. 4A-4B, in conjunction with FIGS. 1A-2, another embodiment of a drive assembly configured for use with forceps 10 for imparting movement of jaw members 110 and 120 between the open position (FIG. 1A) and the closed position (FIG. 1B) upon actuation of handles 30a, 30b between the spaced-apart and approximated positions is shown generally identified by reference numeral 600. Drive assembly 600 is similar to drive assembly 60 (FIGS. 3A-3B) and, thus, only differences therebetween will be described in detail below for purposes of brevity. Further, any of the features of drive assembly 60 (FIGS. 3A-3B) may be used in conjunction with or in place of any of the features of drive assembly 600, and vice versa.

Drive assembly 600 includes a pair of linkages 610, 620 and a pair of cable members 615, 625 that operatively couple handles 30a, 30b to mandrel 640 such that approximation of handles 30a, 30b pulls mandrel 640 proximally, thereby moving jaw members 110, 120 from the open position (FIG. 1A) towards the closed position (FIG. 1B) and such that return of handles 30a, 30b towards the spaced-apart position urges mandrel 640 distally thereby returning jaw members 110, 120 towards the open position (FIG. 1A).

Linkages 610, 620 of drive assembly 600 each define a first end 611, 621 and a second end 612, 622. First ends 611, 621 of linkages 610, 620 are pivotably coupled to handles 30a, 30b, respectively, towards proximal ends 32a, 32b of handles 30a, 30b via pivot pins 613, 623, respectively. Second ends 612, 622 of linkages 610, 620 are pivotably coupled to proximal ends 616, 626 of cable member 615, 625, respectively. Cable members 615, 625 extend from proximal ends 616, 626 thereof distally through housing to distal ends 617, 627 thereof, which are coupled to mandrel 640. Mandrel 640, similarly as detailed above with respect to drive assembly 60 (FIGS. 3A-3B), is engaged to the distal end of drive bar 602. Cable members 615, 625 may be formed as longitudinally resilient cables, spring cables, or other suitable elongate members capable of resiliently expanding/contracting in length. Alternatively, cable members 615, 625 may be substantially rigid in configuration. Cable members 615, 625 may further be slidably disposed within tracks 28a, 28b, respectively, formed within housing 20 to provide support and inhibit cables 615, 625 from substantially bending off-axis. In embodiments where cable members 615, 625 are resiliently expandable/contractable, the spring forces of cable members 615, 625 may be selected such that jaw members 110, 120 impart a closure pressure on tissue grasped therebetween within the range of about 3 kg/cm$^2$ to about 16 kg/cm$^2$, although other closure pressures are also contemplated.

In use, with handles 30a and 30b initially disposed in the spaced-apart position relative to housing 20 and one another, as shown in FIG. 4A, jaw members 110, 120 are disposed in the open position (FIG. 1A). In this position, linkages 610, 620 are disposed in an angled orientation relative to drive bar 602 and, as a result, cable members 615, 625 are disposed in a distal position. As handles 30a, 30b are pivoted inwardly towards one another and housing 20 to close jaw members 110, 120, proximal ends 32a, 32b of handles 30a, 30b are approximated relative to housing 20 and one another, as shown in FIG. 4B. The approximation of handles 30a, 30b towards one another urges first ends 611, 621 of linkages 610, 620 inwardly towards one another. As a result, linkages 610, 620 are pivoted proximally about their first ends 611, 621 towards a more aligned orientation, e.g., towards a parallel orientation, relative to drive bar 602, as shown in FIG. 4B. Movement of linkages 610, 620 in this manner urges second ends 612, 622 of linkages 610, 620 proximally which, in turn, pulls cable members 615, 625 proximally. Proximal pulling of cable members 615, 625 pulls mandrel 640 and drive bar 602 proximally such that jaw members 110, 120 are pivoted from the open position (FIG. 1A) towards the closed position (FIG. 1B) to grasp tissue therebetween. With tissue grasped between jaw members 110, 120, tissue may be treated and/or cut similarly as described above.

Release or return of handles 30a, 30b to the spaced-apart position relative to one another and housing 20 may be effected to return jaw members 110, 120 to the open position (FIG. 1A). In embodiments where cable members 615, 625 are formed as resilient cables, spring cables, or other expanding/contracting members, jaw members 110, 120 may be returned to the open position (FIG. 1A) upon release of handles 30a, 30b and under bias of cable members 615, 625. Alternatively, handles 30a, 30b may be moved back to the approximated position to thereby rotate linkages 610, 620 distally, urge cable members 615, 625 distally, urge mandrel 640 and drive bar 602 distally, and pivot jaw members 110, 120 back to the open position.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
  an end effector assembly movable between a first position and a second position;
  first and second handles, each handle pivotable about a first end thereof and extending to a second end thereof, the second ends of the handles movable relative to one another between a spaced-apart position and an approximated position; and a drive assembly, including:
   a drive bar coupled to the end effector assembly at a distal end of the drive bar such that translation of the drive bar relative to the end effector assembly effects movement of the end effector assembly between the first and second positions;
   a biasing member defining a first end, a second end, and an intermediate portion disposed between the first and second ends, the first end of the biasing member coupled to the first handle adjacent the second end of the first handle, the second end of the biasing member coupled to the second handle adjacent the second end of the second handle, and the intermediate portion of the biasing member coupled to the drive bar, wherein movement of the handles from the spaced-apart position to the approximated position urges the first and second ends of the biasing member towards one another such that the intermediate portion of the biasing member is displaced relative to the first and second ends of the biasing member; and
   a mandrel coupled to the drive bar, the mandrel disposed proximally of the biasing member and in abutting relation with the intermediate portion of the biasing member such that displacement of the intermediate portion urges the mandrel to translate, thereby urging the drive bar to translate relative to the end effector assembly to effect movement of the end effector assembly between the first and second positions.

2. The surgical instrument according to claim 1, wherein the end effector assembly includes a pair of jaw members, at least one of the jaw members movable relative to the other between an open position, corresponding to the first position, and a closed position, corresponding to the second position, for grasping tissue therebetween.

3. The surgical instrument according to claim 2, wherein the biasing member is configured such that a closure pressure within the range of about 3 kg/cm$^2$ to about 16 kg/cm$^2$ is imparted to tissue grasped between the jaw members.

4. The surgical instrument according to claim 2, wherein at least one of the jaw members is adapted to connect to a source of energy for conducting energy through tissue grasped between the jaw members to treat tissue.

5. The surgical instrument according to claim 1, further comprising a housing, the first and second handles pivotably coupled to the housing at the first ends thereof, the second ends of the handles movable relative to one another and the housing between the spaced-apart position and the approximated position.

6. The surgical instrument according to claim 5, further comprising a shaft extending distally from the housing, the end effector assembly disposed at a distal end of the shaft.

7. The surgical instrument according to claim 6, wherein the drive bar extends from the housing distally through the shaft.

8. The surgical instrument according to claim 1, wherein, in the spaced-apart position of the handles, the biasing member defines a proximally-bowed configuration wherein the intermediate portion is proximally offset relative to the first and second ends of the biasing member by a first distance.

9. The surgical instrument according to claim 8, wherein, in the approximated position of the handles, the biasing member is further bowed-proximally such that the intermediate portion is proximally offset relative to the first and second ends of the biasing member by a second distance greater than the first distance.

10. The surgical instrument according to claim 1, wherein the mandrel is coupled to the drive bar towards a proximal end of the drive bar.

11. The surgical instrument according to claim 1, wherein the mandrel is biased towards an initial position, thereby biasing the end effector assembly towards the first position.

* * * * *